US008430926B2

(12) United States Patent
Kirson

(10) Patent No.: US 8,430,926 B2
(45) Date of Patent: Apr. 30, 2013

(54) ANNULOPLASTY WITH ENHANCED ANCHORING TO THE ANNULUS BASED ON TISSUE HEALING

(75) Inventor: E David Kirson, Barrington Hills, IL (US)

(73) Assignee: JAPD Consulting Inc., New York, NY (US)

( * ) Notice: Subject to any disclaimer, the term of this patent is extended or adjusted under 35 U.S.C. 154(b) by 799 days.

(21) Appl. No.: 11/837,077

(22) Filed: Aug. 10, 2007

(65) Prior Publication Data

US 2008/0077235 A1 Mar. 27, 2008

Related U.S. Application Data

(60) Provisional application No. 60/822,113, filed on Aug. 11, 2006.

(51) Int. Cl.
*A61F 2/24* (2006.01)
(52) U.S. Cl.
USPC .......................................... 623/2.37; 623/904
(58) Field of Classification Search .......... 623/2.36–2.4, 623/904; 606/151
See application file for complete search history.

(56) References Cited

U.S. PATENT DOCUMENTS

| | | | | |
|---|---|---|---|---|
| 5,860,951 | A * | 1/1999 | Eggers et al. | 604/510 |
| 6,283,961 | B1 * | 9/2001 | Underwood et al. | 606/41 |
| 6,306,163 | B1 * | 10/2001 | Fitz | 623/1.12 |
| 6,716,243 | B1 * | 4/2004 | Colvin et al. | 623/2.4 |
| 7,314,485 | B2 * | 1/2008 | Mathis | 623/2.37 |
| 7,588,582 | B2 * | 9/2009 | Starksen et al. | 606/139 |
| 2004/0220610 | A1 * | 11/2004 | Kreidler et al. | 606/200 |
| 2005/0107812 | A1 | 5/2005 | Starksen et al. | |
| 2005/0119523 | A1 | 6/2005 | Starksen et al. | |
| 2005/0216078 | A1 | 9/2005 | Starksen et al. | |
| 2005/0273138 | A1 | 12/2005 | To et al. | |
| 2006/0025750 | A1 | 2/2006 | Starksen et al. | |
| 2006/0025784 | A1 | 2/2006 | Starksen et al. | |
| 2006/0025787 | A1 | 2/2006 | Morales et al. | |
| 2006/0058817 | A1 | 3/2006 | Starksen et al. | |
| 2006/0129188 | A1 * | 6/2006 | Starksen et al. | 606/232 |

OTHER PUBLICATIONS

Maniu, MD, et al. Acute & Chronic Reduction of Functional Mitral Regurgitation . . . Journal of the American College of Cardiology, vol. 44, No. 8, pp. 1652-1661 (2004).
Cohn, et al., The Evolution of Mitral Valve Surgery, Am heart Hosp. J. 2003:1 pp. 40-46 (2003).

(Continued)

*Primary Examiner* — Suzette J Gherbi
(74) *Attorney, Agent, or Firm* — Proskauer

(57) ABSTRACT

Methods, delivery systems and engaging apparatuses for the placement and treatment of an insufficient or stenotic cardiac valve, such as the mitral valve are disclosed. One such method is based on a two step procedure, where during the first step the engaging apparatus is brought to the valve annulus using a delivery system which permits continued normal blood flow. In some preferred embodiments, this is implemented with a balloon and other preferred embodiments it is implemented using a multi-pronged structure that is collapsible like an umbrella frame. The second step is performed after the engaging apparatus has been integrated into the annular wall by natural processes of tissue healing and remodeling. In the second step the engaging apparatus is tightened leading to tightening of the valve annulus and correction of existing valvular insufficiency. Optionally, an artificial valve may be anchored to the engaging apparatus during the same or subsequent procedure to correct either valvular insufficiency or stenosis.

16 Claims, 10 Drawing Sheets

OTHER PUBLICATIONS

Damon, et al., Percutaneous Mitral Valve Repair for Chronic Ischemic Mitral Regurgitation.. Journal of the American Heart Association, publ. Apr. 25, 2005.

Felger, M.D., et al., Robot-Assisted Sutureless Minimally Invasive Mitral Valve Repair, Cardiovascular Surgery, Surgical Technology International XII, p. 185-187 (undated).

Folliguet, et al., Mitral valve repair robotic versus sternotomy, European Journal of Cardio-Thoracic Surgery 29 (2006) pp. 362-366.

Greelish et al., Minimally invasive mitral valve repair suggests earlier operations for mitral valve.., The Journal of Thoracic & Cardiovascular Surgery vol. 126, No. 2 (2003).

Desimone, et al., Adjustable Tricuspid Valve Annuloplasty Assisted by Intraoperative Transesophageal . . . The American Journal of Cardiology vol. 71 pp. 926-931 Apr. 15, 1993.

* cited by examiner

US 8,430,926 B2

ANNULOPLASTY WITH ENHANCED ANCHORING TO THE ANNULUS BASED ON TISSUE HEALING

CROSS REFERENCE TO RELATED APPLICATIONS

This application claims the benefit of U.S. provisional application No. 60/822,113, filed Aug. 11, 2006, which is incorporated herein by reference.

BACKGROUND

In the recent past, many advances have been made to reduce the invasiveness of cardiac surgery. In an attempt to avoid open, stopped-heart procedures, which may be accompanied by high patient morbidity and mortality, many devices and methods have been developed for performing surgery on a heart through smaller incisions, operating on a beating heart, and finally, in the past years, performing cardiac procedures via transvascular access. Significant technological advances have been made in various types of cardiac procedures, such as cardiac ablation techniques for treating atrial fibrillation, stenting procedures for atherosclerosis, and valve repair procedures. More specifically, much progress has been made on treating conditions such as mitral valve regurgitation. In implementing many minimally invasive cardiac surgery techniques, especially beating-heart techniques, one of the most significant challenges is positioning a treatment device and once positioned, to effectively deploy and fix a given device or treatment into or on the surface of the target cardiac tissue.

Traditional treatment of heart valve stenosis or regurgitation, such as mitral or tricuspid regurgitation, typically involves an open-heart surgical procedure to replace or repair the valve. Valve repair procedures typically involve annuloplasty, a set of techniques designed to restore the valve annulus shape and strengthen the annulus. Conventional annuloplasty surgery generally requires a thoracotomy, and sometimes a median sternotomy. These open heart procedures involve placing the patient on a cardiopulmonary bypass machine for sustained periods so that the patient's heart and lungs can be artificially stopped during the procedure. Finally, valve repair and replacement procedures are technically challenging and require a relatively large incision through the wall of the heart to access the valve.

Due to the highly invasive nature of open heart valve repair or replacement, high risk patients are usually not candidates for these procedures and thus are destined to functional deterioration and cardiac enlargement. Often, such patients have no feasible alternative treatments for their heart valve conditions.

In order to try and solve this problem, a number of devices and methods for repairing cardiac valves in a less invasive manner have been described. Some devices offer heart valve repair through minimally invasive incisions or intravascularly, while others attempt to improve open heart surgical procedures on beating hearts, stopped hearts or both. Difficulties in performing minimally invasive intra-cardiac surgery include positioning a minimally invasive treatment device in a desired location for performing a procedure and effectively placing and fixing a device into or on the surface of the target cardiac tissue. In heart valve repair procedures, for example, it is often essential for a physician to fix a device to valve annulus tissue. Annular tissue tends to be more fibrous than surrounding muscular or valve leaflet tissue, thus providing a more suitable location for securing such a device. In the past, various types of anchors and anchoring techniques have been developed in order to fix treatment devices to the annular tissue. This is an important stage in all annuloplasty procedures and especially in procedures for treating mitral or tricuspid valve regurgitation.

Devices and methods that address these difficulties are described in U.S. patent application Ser. Nos. 60/445,890, 60/459,735, 60/462,502, 60/524,622, 10/461,043, 10/656, 797 and Ser. No. 10/741,130. For example, these references describe devices and methods for exposing, stabilizing and/or performing procedure on a heart valve annulus, such as a mitral valve annulus. Many of these methods and devices have shown preliminary promise, however a highly safe and effective method and engaging apparatus for performing cardiac valve annuloplasty has, until now, been lacking.

DETAILED DESCRIPTION OF THE PREFERRED EMBODIMENTS

Figure 1:
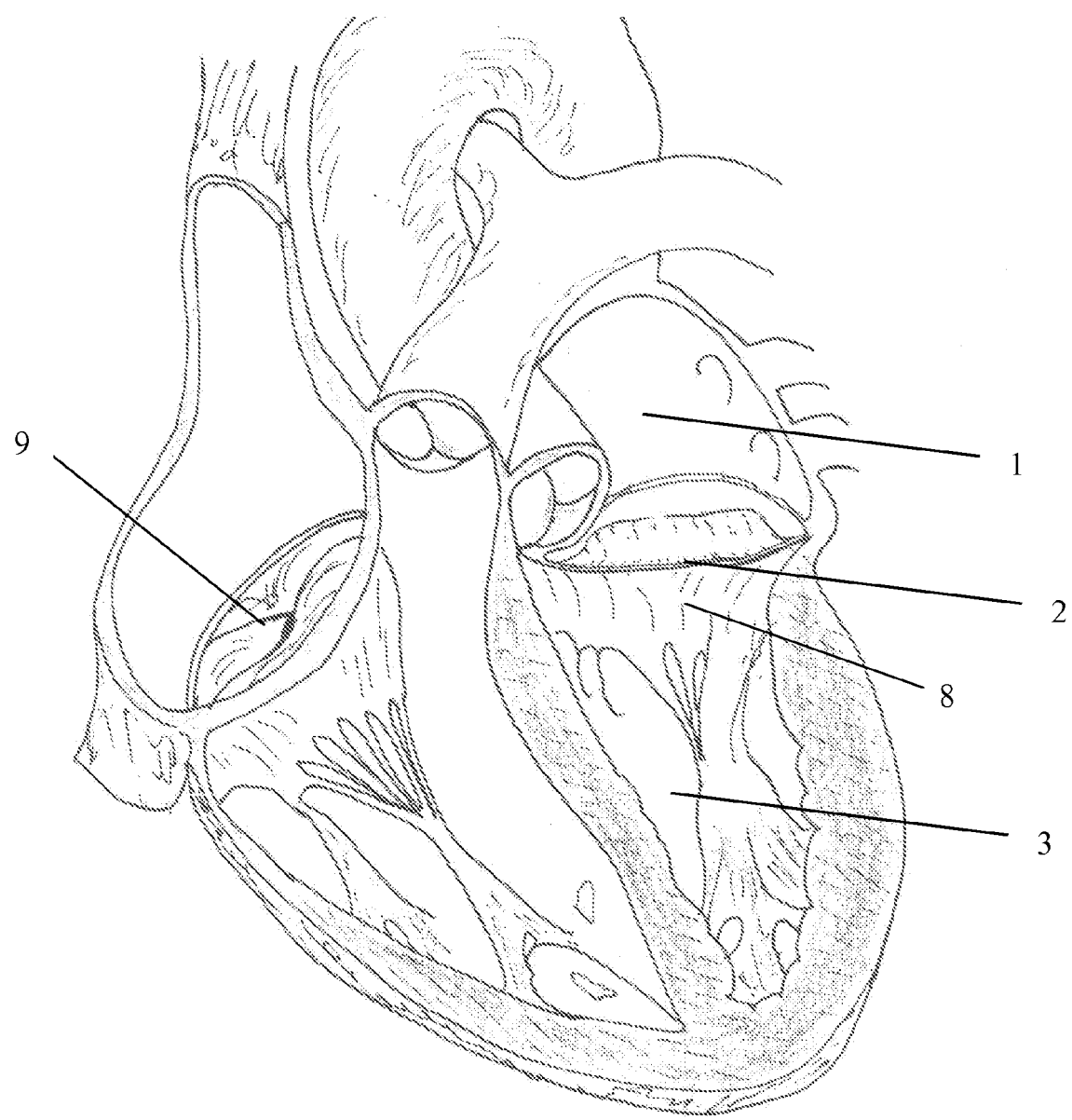
FIG. 1 shows the location of the mitral annulus in a cross-section of the heart.

FIG. 1 shows the location of the mitral annulus 2 in a cross-section of the heart. The method and engaging apparatus of the current delivery system are used to facilitate transvascular, minimally invasive and other "less invasive" surgical procedures, by facilitating the placing and fixing of a treatment engaging apparatus 6 at a treatment site. As used herein, "less invasive" means any procedure that is less invasive than traditional, large-incision, open surgical procedures. Generally, any procedure in which a goal is to minimize or reduce invasiveness to the patient may be considered less invasive. Although the methods described herein are developed for use in minimally invasive procedures, they may be applied to performing or enhancing any suitable procedure, including traditional open heart surgery. The present application describes methods and apparatuses for performing heart valve repair or replacement procedures, and more specifically heart valve annuloplasty procedures such as mitral valve annuloplasty to treat mitral regurgitation and mitral valve replacement to treat mitral stenosis. In other embodiments, the devices and methods may be used to enhance a laparoscopic or other endoscopic procedure on any part of the body, such as the bladder, stomach, gastroesophageal junction, vasculature, gall bladder, or the like. Therefore, although the following description typically focuses on mitral valve 8 and other heart valve 9 repair, such description should not be interpreted to limit the scope of the invention.

Figure 2:
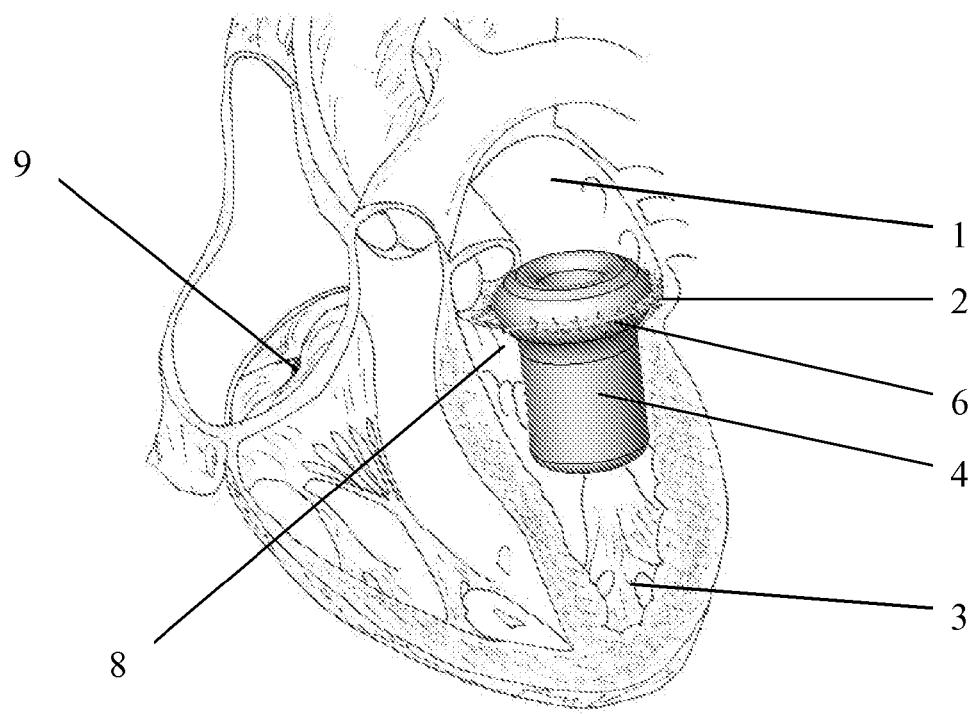
FIG. 2 shows a first approach for positioning a first embodiment of an engaging apparatus at the annulus.

FIG. 2 shows a cross-section of the heart, with a full view of one embodiment of a balloon delivery system 4 and a full view of an engaging apparatus 6. The balloon delivery system 4 can be used for placement of the engaging apparatus 6 at the annulus 2. Initially, the balloon is routed to the proper position in its deflated state (not shown) using any suitable route or method (e.g., an endoscopic technique), and then inflated. At this point, the system will resemble FIG. 2, in which the balloon 4 is shown in its inflated state, positioned at the mitral valve 8. The engaging apparatus 6 is located around the balloon 4, and the inflation brings the engaging apparatus 6 into proximity of the annular tissue 2 and presses them towards each other. The engaging apparatus 6 initially surrounds the balloon 4 and anchors to the annular tissue 2 upon inflation of the balloon 4.

Figure 3:
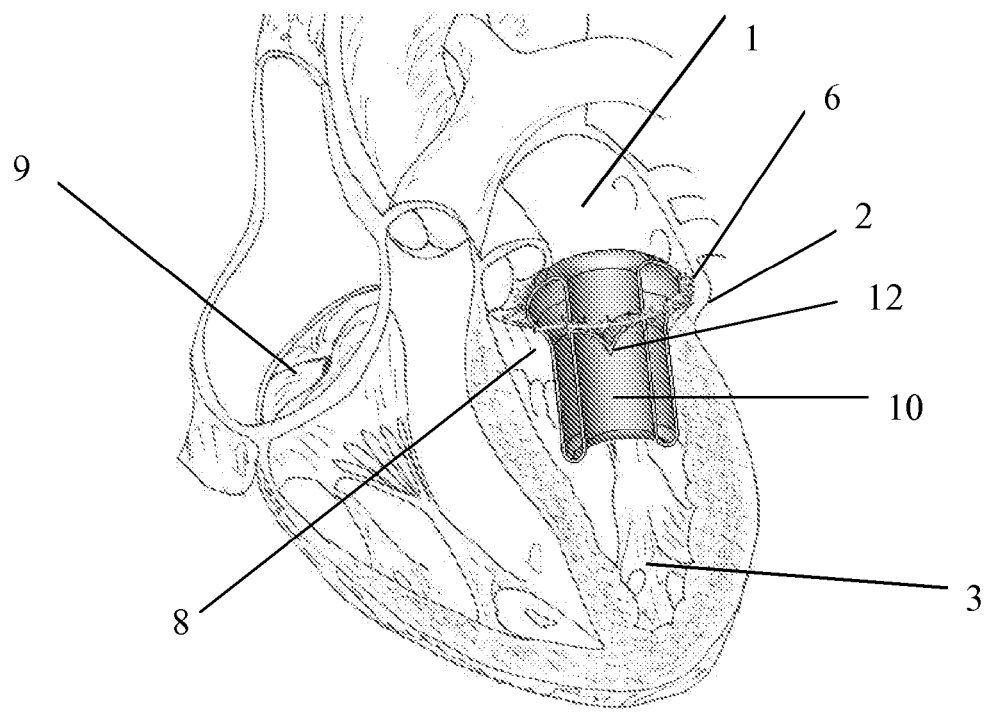
FIG. 3 shows a cross section of the embodiment shown in FIG. 2.

FIG. 3 depicts the same items as FIG. 2 except that the delivery system is shown in cross section. The balloon is shown with a central channel 10 and flexible leaflets 12 seen within its lumen. These leaflets 12 act as a temporary replacement valve in order to allow normal heart function during the insertion procedure. In some embodiments, valve repair or replacement may be implemented using a hollow, inflatable balloon 4 with integral flexible valve leaflets 12 within its lumen which act as a temporary replacement for the natural valve upon inflation, while maintaining adequate flow through from the atrium 1 to the ventricle 3 throughout the procedure via channel 10. Because of the channel 10, blood can flow through the system even when the balloon 6 is inflated, which facilitates installation of the device into a beating heart.

Upon deflation of the balloon, the engaging apparatus 6 will detach from the balloon 4 and remain attached to the annulus 2 with enough anchoring force to withstand normal cardiac contraction, flow and valve movement. Attachment to the annulus can be aided by using appropriate anchors, hooks, barbs, etc. Alternatively, the engaging apparatus 6 can hold itself in place by exerting a centripetal pressure on the annulus, generated by the springiness of the engaging apparatus.

In some embodiments (not shown), the engaging apparatus 6 may be contained within a hidden circumferential pocket surrounding the balloon 4 and will engage the annular tissue 2 only upon release from this pocket. The release of the engaging apparatus 6 from the balloon 4 may be performed by releasing a slip-knot like suture from the balloon 4 or any other suitable alternative approach. In these embodiments, conventional balloon and balloon inflation technology may be used, similar to those used in other annuloplasty procedures (e.g., conventional balloon procedures for widening a stenotic valve).

Figure 4:
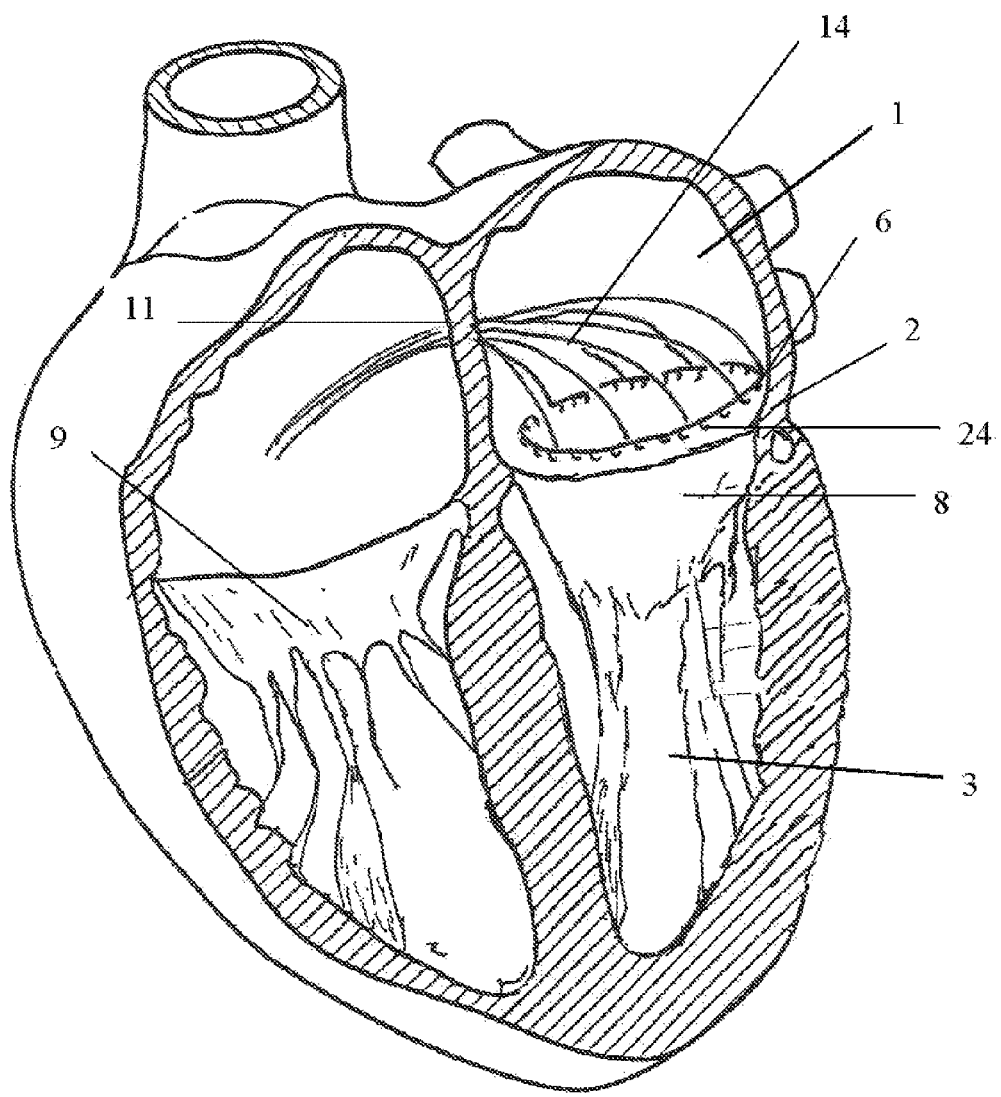
FIG. 4 shows an embodiment of a delivery system in which a multi-pronged device is used to place the engaging apparatus at the annulus.

FIG. 4 shows a cross-section of the heart, a full view of the first embodiment of an engaging apparatus 6, and a full view of the second embodiment of a delivery system. This delivery system uses a multi-pronged device 14 that is preferably collapsible (similar to an umbrella frame, a truncated wire whisk, etc). to place the engaging apparatus 6 at the annulus 2. The methods and engaging apparatus of the delivery system, however, may be used in any suitable procedure, both cardiac and non-cardiac. For example, they may be used in procedures to repair any heart valve 9, to replace any heart valve 9, to repair an atrial-septal 11 defect, to access and possibly perform a valve repair from (or through) the coronary sinus.

Figure 5:
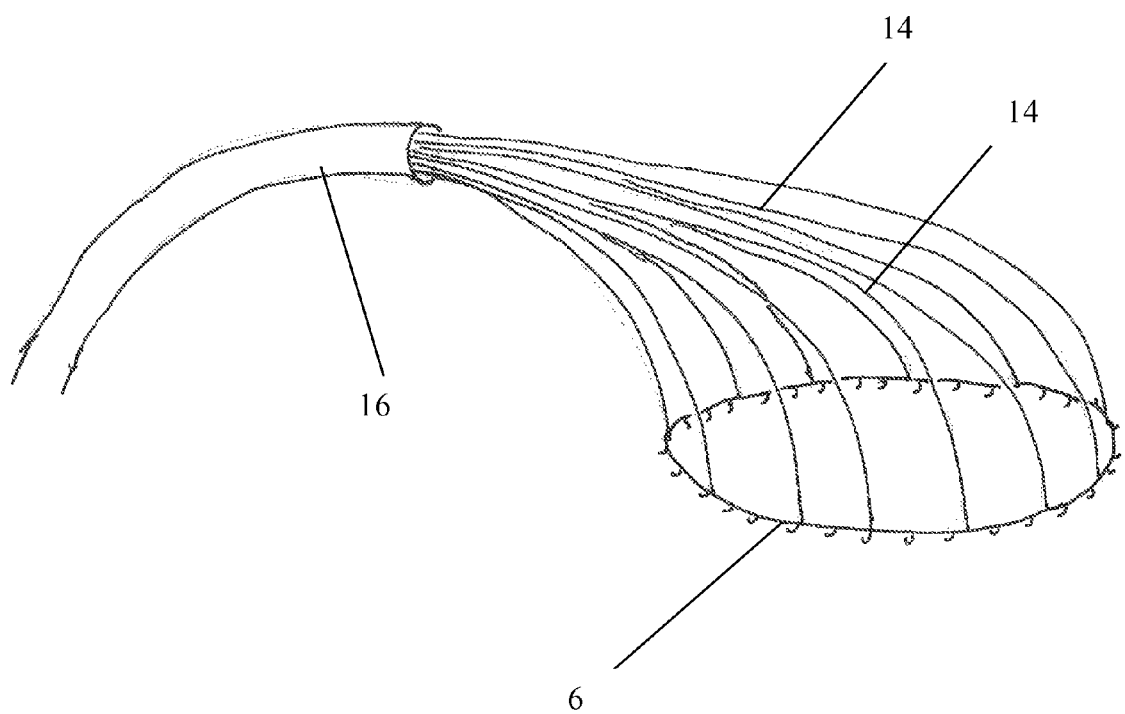
FIG. 5 shows a close up of the end of the FIG. 4 embodiment.

FIG. 5 shows a detail view of the multi-pronged delivery system 14 shown in FIG. 4. In some embodiments, valve repair may be implemented using a delivery device 14 which can be extended from the tip of a catheter 16 to allow for the correct positioning of the engaging apparatus 6 at the annulus. The multi-pronged placement device 14 can be introduced into the left atrium 1 (shown in FIG. 4) during on-pump or off-pump procedures through the wall of the atrium or through the intra-atrial septum, with the catheter 16 introduced by intravascular or minimal invasive approach. Placement and tightening may be performed on a beating heart because blood can flow through the spaces between the prongs. Access to the beating heart may be accomplished by any available technique, including intravascular, trans-thoracic, and the like. Intravascular access to a heart valve may be achieved using any suitable route or method.

For example, to perform a procedure on a mitral valve 8 a catheter 16 may be advanced through a femoral artery, to the aorta, and into the left ventricle of the heart, to contact a length of the mitral valve. After it is so positioned, the device 14 is expanded so as to press the engaging apparatus 6 against the annulus. The expansion of the delivery system 14 may be implemented using any suitable technique such as withdrawal of a sheath that permits the prongs to to spring out to their natural state. Alternatively, access may be gained through the venous delivery system, to a central vein, into the right atrium of the heart, and across the inter-atrial septum to the left side of the heart to contact a length of the mitral valve. In alternative embodiments, the catheter device 16 may access the coronary sinus and a valve procedure may be performed directly from the sinus. Furthermore, in addition to beating heart access, methods of the present delivery system may be used for intravascular stopped heart access as well as stopped heart open chest procedures. Any suitable intravascular or other access method may be substituted.

Figure 6:
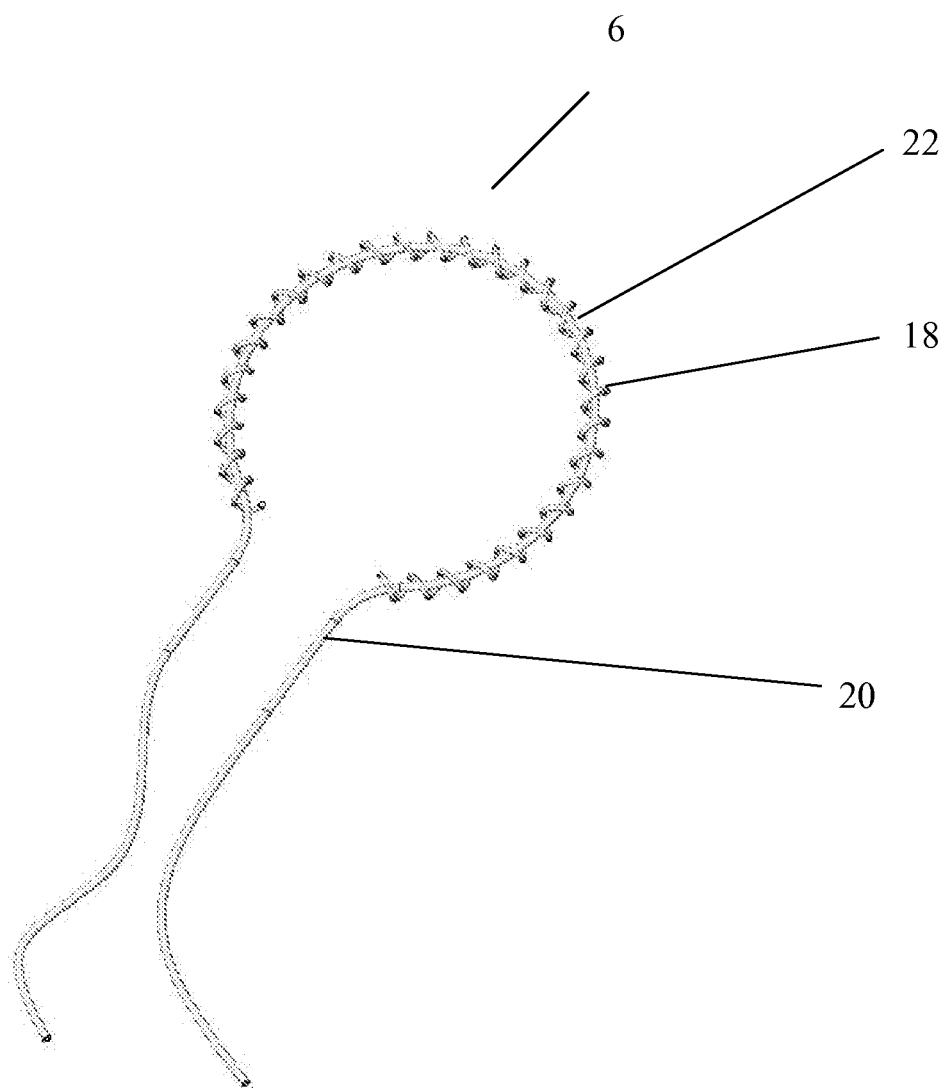
FIG. 6 is a detailed view of the first embodiment of the engaging apparatus.

FIG. 6 shows a detailed view of the first embodiment of the engaging apparatus. This embodiment uses a helical spring 18 that has been formed to be substantially arc-shaped preferably subtending an arc of at least 180°, and more preferably at least 270°, with a wire 20 within it for subsequent tightening. The spring geometry allows for changes in ring diameter, and creates a channel for the tightening wire. It also allows for tissue healing into the spaces in the spring 22, thereby bonding the engaging apparatus to the annulus wall by embedding the engaging apparatus within the annulus wall. Some time after the initial placement, a second procedure for tightening the engaging apparatus 6 is preferably implemented.

Tightening of the engaging apparatus may be accomplished, for example, by retracting a wire 20 left within the engaging apparatus 6 during its placement at the annulus using a minimally invasive approach. However, any alternative method or device for the tightening of a structure at the annulus may be used. This includes, but is not limited to, different types of steerable catheter tips 16 (as shown in FIG. 4) catheters allowing for direct manipulation of objects at the tip, catheters allowing for visualization of the annulus, and catheters which deliver energy at the area of interest (ultrasound, heat, radiofrequency fields, etc.). Non-invasive techniques for tightening the engaging apparatus 6 may also be used, including but not limited to magnetic manipulation through the chest wall, radiofrequency energy delivery through the chest wall and ultrasound energy transmitted through the chest wall.

The engaging apparatus 6 may be made of Stainless Steel, Nitinol, Elgiloy or Titanium; however any material with the necessary strength, flexibility and biocompatibility to withstand cardiac pressures may be used. A suitable diameter for the arc is between about 25 and about 60 mm. A suitable diameter for the helix is between about 1 and about 3 mm, and a suitable pitch for the helix is between about 1 and about 3 mm.

In some embodiments, the engaging apparatus 6 may be constructed of a spring like ring 18 with or without a central cavity for a tightening wire 20. This spring like ring 18 may be configured to facilitate the growth of annular tissue into the engaging apparatus 6 strengthening the adhesion between the annulus and the engaging apparatus 6. However, other surface geometries which facilitate tissue anchoring into the engaging apparatus may also be used, including but not limited to serrated, hooked, porous or folded surfaces. A tube with holes or serrations cut therein (not shown) may also be used.

In some embodiments, the tightening wire 20 may be made of silk or plastic, however, any material with sufficient strength, elasticity and biocompatibility may be used for this purpose. As used herein, the term "wire" includes all such materials and constructions. The wire 20 may be used for subsequent tightening of the engaging apparatus 6 (e.g., by pulling on both ends of the wire) leading to a tightening of the annulus of the patient's heart.

Figure 7:
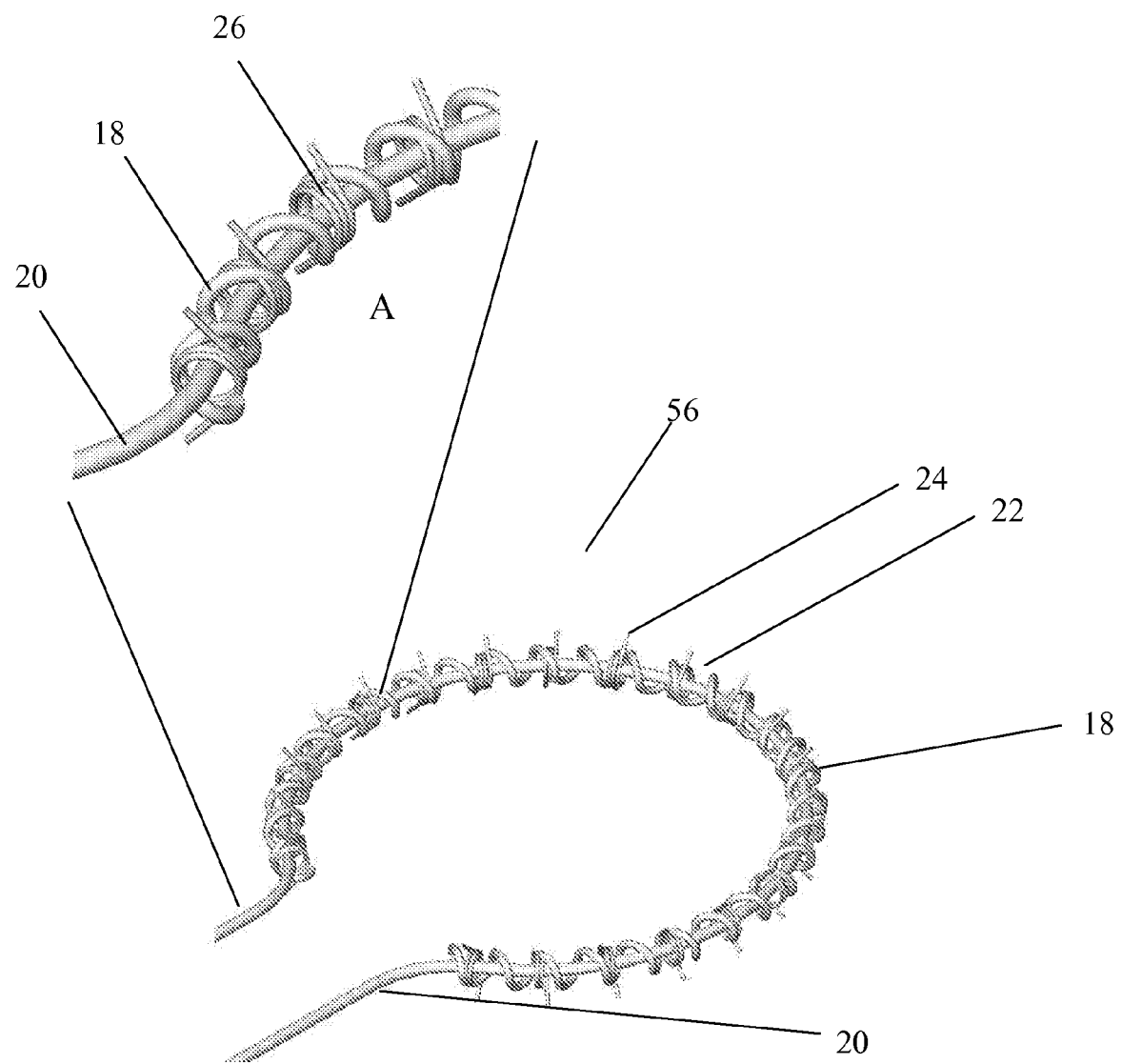
FIG. 7 shows a detailed view of another embodiment of the engaging apparatus.

FIG. 7 shows a detailed view of a second embodiment of an engaging apparatus. This embodiment is similar to the FIG. 6 embodiment discussed above, but anchors 24 are added to the spring like ring 18 for initial anchoring of the engaging apparatus 56 to the annulus to better withstand cardiac contraction, valve motion and blood flow. One type of anchoring element—a two pronged, open ended miniature spring 26—is shown in the insert A, but alternative anchors may be used instead. Any of the delivery systems described above may be used to position the engaging apparatus 56 at the annulus and fix it in place by gentle centripetal pressure 4 alone or in conjunction with any existing placing and anchoring technique or by the use of existing placing and anchoring techniques alone. Alternatively, the engaging apparatus 56 may be placed using any other minimally invasive or invasive placement delivery systems.

Optionally, any of the engaging apparatuses described herein may be coated with an adhesive substance to facilitate integration between the engaging apparatus and the annulus. Optionally, the engaging apparatus may contain hooks, serrations, spokes or sutures for preliminary attachment to the annulus. Examples of suitable structures include, but are not limited to, a closed circular spring with a flexible diameter, open ended semi-circular structures, non circular structures capable of approximation between two or more free tips, and non-continuous structures such as individual tubes connected to the annular rim. Optionally, the engaging apparatus may be made of or elute materials which stimulate or accelerate tissue growth. These materials may include but are not limited to growth factors, pro-inflammatory agents, foreign substances which are immunogenic and lead to an enhanced tissue reaction to the engaging apparatus. Optionally, the engaging apparatus may contain an active electromechanical element, such as a motor or actuator, capable of tightening the engaging apparatus. This active component may be self powered by a battery or by mechanical energy generated by the cardiac muscle or blood flow. The active element may be activated using minimally invasive techniques or non-invasive techniques. In the case of non-invasive activation of the active element, any form of transmitted energy may be used, including but not limited to ultrasound and radiofrequency transmission.

The delivery systems and engaging apparatuses described herein may be used for repair of a cardiac valve annulus such as a mitral valve annulus using a two step procedure: placing and tightening. The method preferably involves bringing an engaging apparatus into position to the annulus of interest as shown in FIG. 2 or FIG. 4 through a minimally invasive procedure.

Figure 8:
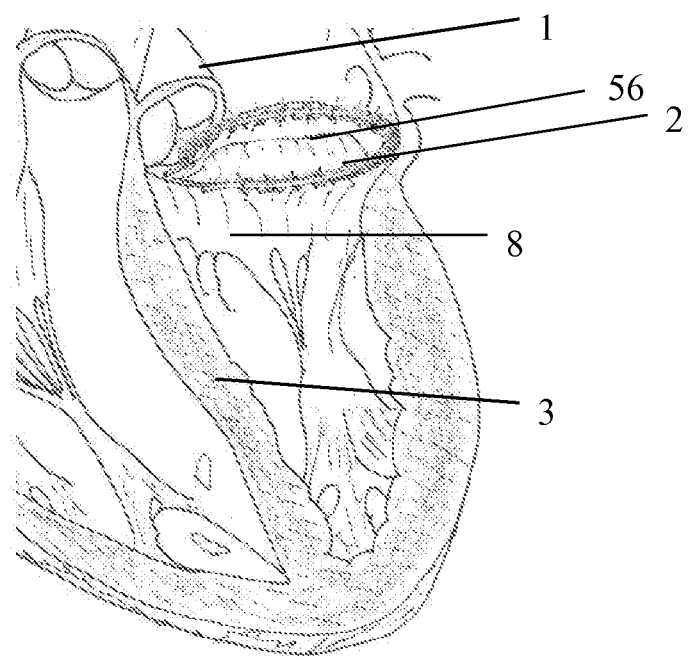
FIG. 8 shows the engaging apparatus of FIG. 7 in location at the mitral annulus immediately after being positioned and anchored to the tissue.

FIG. 8 shows the engaging apparatus 56 from FIG. 7 in location at the mitral annulus 2 immediately after being left in place and anchored to the tissue using the delivery system described above or any other minimally invasive or invasive placement delivery system. No tissue healing or remodeling has occurred at this stage and the engaging apparatus 6 is attached to the annulus 2 with the minimal necessary force.

Figure 9:
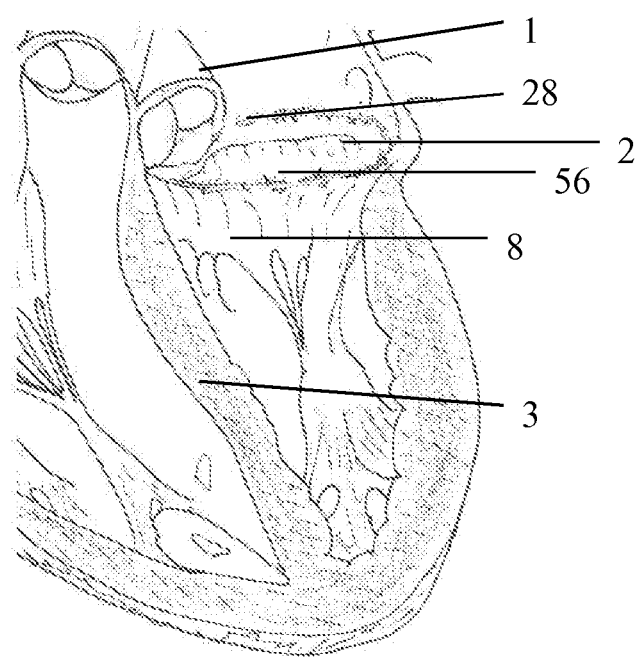
FIG. 9 shows the engaging apparatus of FIG. 7 after being left in place for sufficient time for tissue healing and remodeling to occur.

FIG. 9 shows the same engaging apparatus 56 after being left in place for sufficient time for tissue healing and remodeling to occur 28. At this point the engaging apparatus 56 is integrated into the annulus 2 due to tissue healing which has embedded the engaging apparatus within the annular wall. This tissue healing 28 embeds the engaging apparatus 56 within the wall of the annulus 2 with sufficient integration to allow for subsequent tightening of the engaging apparatus 56 (e.g., by pulling on both ends of the wire 20, shown in FIG. 7) to circumferentially tighten the annulus 2. The anchoring strength of the engaging apparatus to the annulus at this stage is preferably sufficient to withstand tightening of the engaging apparatus 56 and the entire annulus 2 in a subsequent procedure.

By using this procedure (i.e., install, wait for incorporation, then tighten), the initial placement of the engaging apparatus 56 at the annulus 2 requires anchoring strength much lower than that used for existing minimally invasive annuloplasty techniques. The initial anchoring strength is sufficient to withstand the normal shear-forces, flow and contraction of the beating heart but, may be less than that necessary for tightening the annulus 2. The tightening procedure is subsequently performed during a second procedure after allowing a sufficiently long period of time for tissue remodeling 28 into and around the engaging apparatus. It is expected that one week should be sufficient, but it may be possible to use a shorter waiting time in some circumstances.

Alternatively, in embodiments that rely on adhesion the second step of tightening the engaging apparatus 56 may be performed during the same procedure after allowing sufficient time for adhesion to occur between the engaging apparatus 56 and the annular tissue 2. The tightening procedure may also be performed in any number of subsequent procedures or non-invasively through the chest wall. Optionally, the engaging apparatus 56 may deliver energy or focus externally transmitted energy to the annular surface 2 in order to accelerate tissue growth into or around the engaging apparatus 28.

Figure 10:
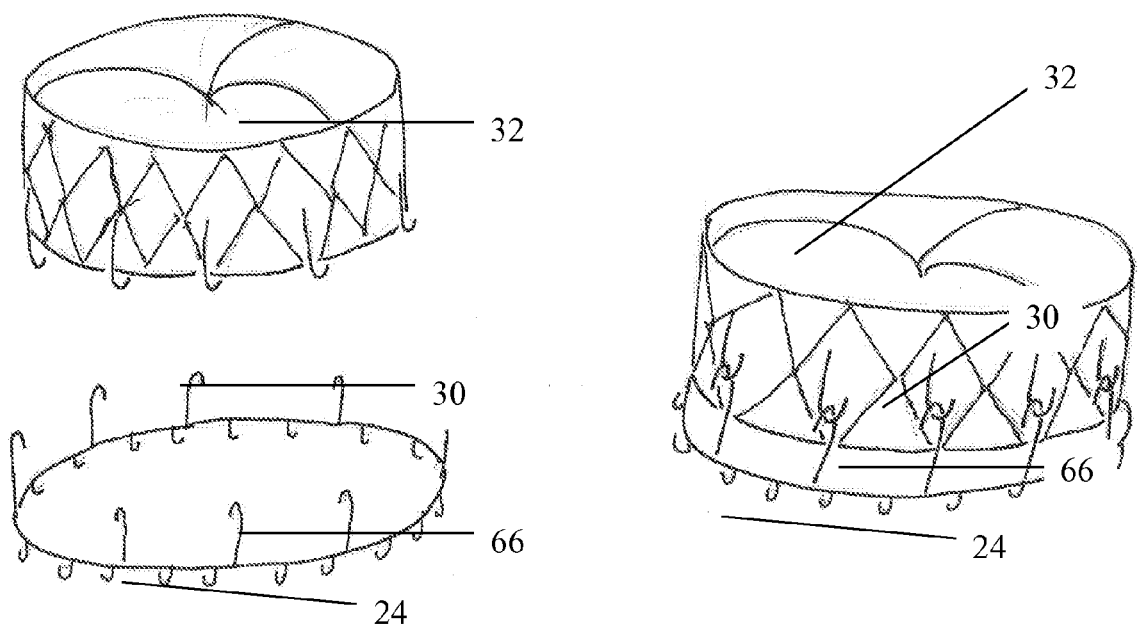
FIG. 10 shows another embodiment of an engaging apparatus that contains an integral anchoring delivery system.

FIG. 10 shows yet another embodiment in which the engaging apparatus 66 contains an integral anchoring delivery system 30 which allows for an artificial valve 32 to be connected to the engaging apparatus 66, during a subsequent procedure, instead of or in addition to tightening of the annulus. The illustrated delivery system may be used for replacement of a cardiac valve, such as the mitral valve using a three step procedure: widening of the annulus, placing the engaging apparatus 66, and anchoring an artificial valve 32 to the engaging apparatus 66. Introduction of the artificial valve 32 to the engaging apparatus may be performed through an intravascular or minimally invasive approach.

Figure 11:
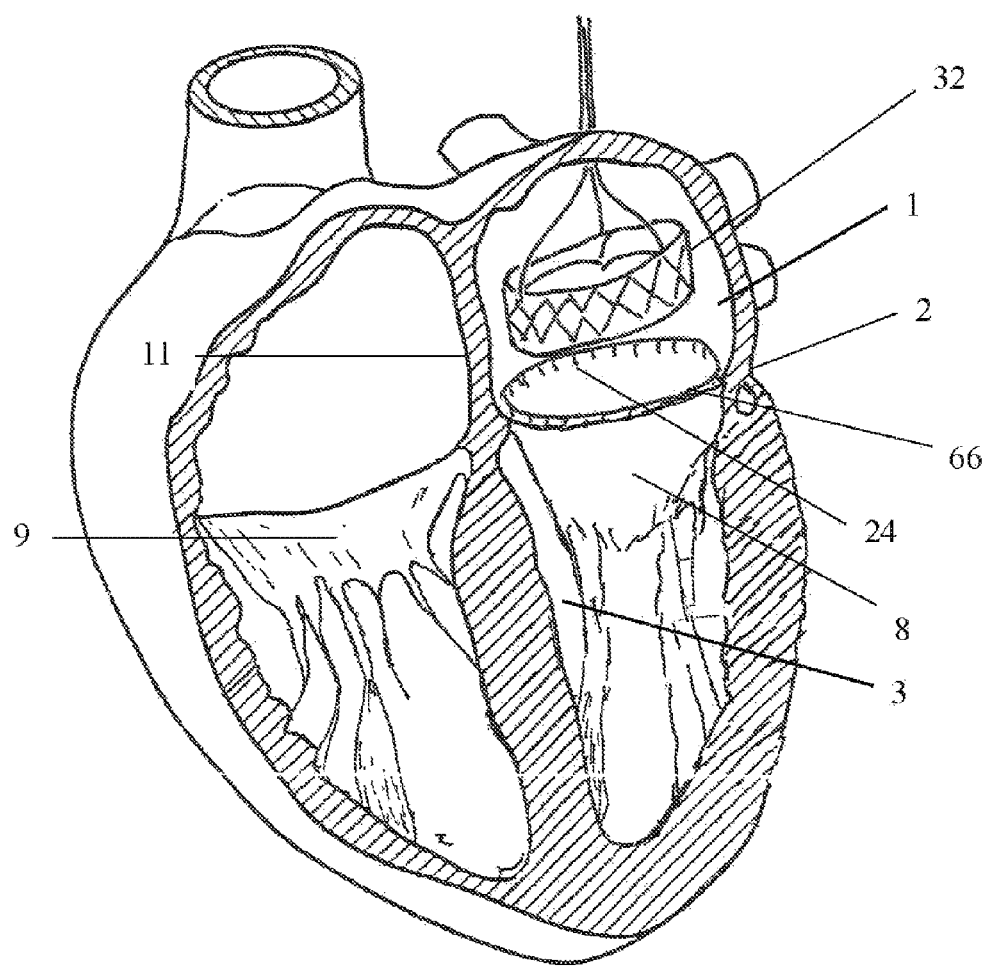
FIG. 11 shows the FIG. 10 embodiment with an artificial valve anchored to the engaging apparatus.

FIG. 11 shows the FIG. 10 embodiment where the artificial valve 32 is anchored to the engaging apparatus 66 during a subsequent, minimally invasive procedure. Optionally, the engaging apparatus 66 may be placed at the annulus 2 as a second step procedure following widening of the annulus 2 and valve 8 using a minimally invasive balloon inflation technique or any other method for widening a stenotic valve. Subsequently, the artificial valve 32 may be attached to the engaging apparatus 66 during a third procedure, instead of or in addition to tightening of the annulus 2.

All of the above-described embodiments advantageously permit blood flow during insertion of the delivery system and the engaging apparatus.

I claim:

1. A method of tightening an annulus of a heart comprising the steps of:
    pressing an engaging apparatus with a contractible diameter up against an inner surface of the annulus, wherein the engaging apparatus is configured to attach to the inner surface with an initial anchoring strength when pressed against the inner surface, wherein the initial anchoring strength is less than that necessary to withstand tightening;
    waiting for a bond to develop between the engaging apparatus and the annulus based on tissue healing and remodeling into and around the engaging apparatus that is strong enough to withstand tightening; and
    contracting the engaging apparatus after development of the bond based on tissue healing and remodeling.

2. The method of claim 1, wherein the pressing step comprises the step of inflating a balloon-like object to press the engaging apparatus against the inner surface of the annulus, and wherein the balloon-like object has a channel that permits blood to flow therethrough during the pressing step.

3. The method of claim 1, wherein the pressing step comprises the step of opening a truncated wire-whisk shaped structure configured to press the engaging apparatus against the inner surface of the annulus, and wherein blood is free to flow past the truncated wire-whisk shaped structure during the pressing step.

4. The method of claim 1, wherein the step of waiting for a bond to develop between the engaging apparatus and the annulus comprises waiting for at least one week.

5. The method of claim 1, wherein the engaging apparatus has an annulus contact portion that is shaped like a helical spring that has been formed to be substantially arc-shaped, with an arc that subtends at least 270°.

6. An apparatus for repairing an annulus comprising:
    an annulus contact portion having an outer boundary that is configured for pressing outwards against the annulus, wherein the annulus contact portion is substantially arc-shaped and has an inner core, and wherein the annulus contact portion is configured to attach to the annulus with an initial anchoring strength when pressed against the annulus, the initial anchoring strength being less than that necessary to withstand tightening, and wherein the annulus contact portion is also configured to permit tissue healing and remodeling into and around the annulus contact portion that increases the anchoring strength over time;
    a truncated wire-whisk shaped structure configured to press the annulus contact portion against the inner surface of the annulus while permitting blood to flow freely past the truncated wire-whisk shaped structure; and
    a wire that runs through the inner core and is arranged with respect to the annulus contact portion so that pulling on the wire causes the outer boundary to contract.

7. The apparatus of claim 6, wherein the annulus contact portion has a plurality of barbs configured to promote initial anchoring of the annulus contact portion to the annulus.

8. The apparatus of claim 6, wherein the substantially arc-shaped annulus contact portion subtends an angle of at least 180°.

9. The apparatus of claim 6, wherein the substantially arc-shaped annulus contact portion subtends an angle of at least 270°.

10. The apparatus of claim 6, wherein annulus contact portion comprises a helical spring that has been formed into an arc.

11. The apparatus of claim 10, wherein the helical spring has an outer diameter between about 25 and about 60 mm, a helix diameter between about 1 and about 3 mm, and a helix pitch between about 1 and about 3 mm.

12. The apparatus of claim 10, wherein the annulus contact portion has a plurality of barbs configured to promote attachment of the annulus contact portion to the annulus.

13. The apparatus of claim 10, wherein the substantially arc-shaped annulus contact portion subtends an angle of at least 180°.

14. The apparatus of claim 10, wherein the substantially arc-shaped annulus contact portion subtends an angle of at least 270°.

15. The method of claim 3, wherein the step of waiting for a bond to develop between the engaging apparatus and the annulus comprises waiting at least one week.

16. The method of claim 3, wherein the engaging apparatus has an annulus contact portion that is shaped like a helical spring that has been formed to be substantially arc-shaped, with an arc that subtends at least 270°.

* * * * *